US008551919B2

(12) United States Patent
Bais et al.

(10) Patent No.: US 8,551,919 B2
(45) Date of Patent: Oct. 8, 2013

(54) METHODS FOR PROMOTING PLANT HEALTH

(75) Inventors: Harsh Bais, Newark, DE (US); Thimmaraju Rudrappa, Hyderabad (IN)

(73) Assignee: University of Delaware, Newark, DE (US)

( * ) Notice: Subject to any disclaimer, the term of this patent is extended or adjusted under 35 U.S.C. 154(b) by 569 days.

(21) Appl. No.: 12/758,361

(22) Filed: Apr. 12, 2010

(65) Prior Publication Data

US 2010/0260735 A1 Oct. 14, 2010

Related U.S. Application Data

(60) Provisional application No. 61/168,778, filed on Apr. 13, 2009.

(51) Int. Cl.
*A01N 37/00* (2006.01)
(52) U.S. Cl.
USPC .......................................... 504/307; 504/320
(58) Field of Classification Search
None
See application file for complete search history.

(56) References Cited

U.S. PATENT DOCUMENTS

| | | | |
|---|---|---|---|
| 5,809,693 | A | 9/1998 | Chet |
| 6,896,883 | B2 | 5/2005 | Bergstrom et al. |
| 2004/0097372 | A1* | 5/2004 | Abraham et al. ............. 504/127 |
| 2008/0274528 | A1 | 11/2008 | Dixon |
| 2010/0093538 | A1 | 4/2010 | Gnanamanickam |
| 2011/0212835 | A1 | 9/2011 | Bais |
| 2012/0122684 | A1 | 5/2012 | Bais |

FOREIGN PATENT DOCUMENTS

| | | |
|---|---|---|
| JP | 10004954 A | 1/1998 |
| WO | WO-9520040 | 7/1995 |
| WO | WO 2011/109395 A2 | 9/2011 |
| WO | WO 2012/067668 A1 | 5/2012 |

OTHER PUBLICATIONS

Bais et al., Biocontrol of *Bacillus subtilis* against Infection of *Arabidopsis* Roots by *Pseudomonas syringae* Is Facilitated by Biofilm Formation and Surfactin Production, Plant Physiology, vol. 134, (2004), pp. 307-319.
Cavaglieri et al., Biocontrol of *Bacillus subtilis* Against *Fusarium verticillioides* In Vitro and At the Maize Root Level, Research in Microbiology, vol. 156, (2005), pp. 748-754.
Gordillo et al., Motility and Chemotaxis of *Pseudomonas* sp. B4 Towards Polychlorobiphenyls and Chlorobenzoates, FEMS Microbiol Ecol, vol. 60, (2007), pp. 322-328.
Hoekenga et al., AtALMT1, Which Encodes a Malate Transporter, Is Identified As One of Several Genes Critical for Aluminum Tolerance in *Arabidopsis*, PNAS, vol. 103, No. 25, (2006), pp. 9738-9743.

Katagiri et al., The *Arabidopsis thaliana-Pseudomonas syringae* Interaction, American Society of Plant Biologists, The Arabidopsis Book, First Published on Mar. 27, 2002; doi: 10.1199/tab.0039, pp. 1-35.
Kobayashi et al., Characterization of AtALMT1 Expression in Aluminum-Inducible Malate Release and Its Role for Rhizotoxic Stress Tolerance in *Arabidopsis*, Plant Physiology$^{1[W][OA]}$, vol. 145, (2007), pp. 843-852.
Ramos et al., Fermentative Metabolism of *Bacillus subtilis* : Physiology and Regulation of Gene Expression, Journal of Bacteriology, vol. 182, No. 11, (2000), pp. 3072-3080.
Rudrappa et al., A Degradation Product of the Salicylic Acid Pathway Triggers Oxidative Stress Resulting in Down-Regulation of *Bacillus subtilis* Biofilm Formation on *Arabidopsis thaliana* roots, Planta (2007), vol. 226, pp. 283-297.
Rudrappa et al., The Rhizobacterial Elicitor Acetoin Induces Systemic Resistance in *Arabidopsis thaliana*, Communicative & Integrative Biology, vol. 3, No. 2, (2010), pp. 1-9.
Rudrappa et al., Causes and Consequences of Plant-Associated Biofilms, FEM Microbiol, Ecol, vol. 64, (2008), pp. 153-166.
Rudrappa et al., Root-Secreted Malic Acid Recruits Beneficial Soil Bacteria$^{1[C][W][OA]}$, American Society of Plant Biologists, Plant Physiology, vol. 148, (2008), pp. 1547-1556.
Ryu et al., Bacterial Volatiles Induce Systemic Resistance in *Arabidopsis*, American Society of Plant Biologists, Plant Physiology, vol. 134, (2004), pp. 1017-1026.
Scott et al., Salicylate Accumulation Inhibits Growth At Chilling Temperature in *Arabidopsis*, American Society of Plant Biologists, Plant Physiology, vol. 135, (2004), pp. 1040-1049.
International Application Serial No. PCT/US2011/026693, International Search Report and Written Opinion mailed on Jan. 2, 2012, 8 pgs.
U.S. Appl. No. 13/037,880, filed Mar. 1, 2011, 24 pgs.
U.S. Appl. No. 13/037,919, filed Mar. 1, 2011, 20 pgs.
International Application Serial No. PCT/2011/026683, International Search Report and Written Opinion mailed on Dec. 15, 2011, 14 pgs.
Fall, Ray, "A Simple Method to Isolate Biofilm-Forming *Bacillus subtilis* and Related Species From Plant Roots", System. Appl. Microbiol. 27, (Nov. 17, 2003), 372-379.
Khalid A., "Screening Plant Growth-Promoting Rhizobacteria for Improving Growth and Yield of Wheat", Journal of Applied Microbiology (2004), 473-480.

(Continued)

*Primary Examiner* — Alton Pryor
(74) *Attorney, Agent, or Firm* — Mueting, Raasch & Gebhardt, P.A.

(57) ABSTRACT

A method for promoting the health of a plant comprises administering malic acid to the plant or the soil in an amount effective to recruit plant growth promoting rhizobacteria (PGPR) to the plant. Administration of malic acid promotes biofilm formation of PGPR on the plant's roots, thereby restricting entry of a foliar pathogen through stomatal pores present in the leaves. Another method for promoting the health of a plant comprises administering acetoin to the plant or the soil in an amount effective to increase pathogen resistance in aerial parts of the plant.

6 Claims, No Drawings

(56) References Cited

OTHER PUBLICATIONS

Lucy, M., "Applications of Free Living Plant Growth-Promoting Rhizobacteria", Antonie Van Leeuwenhoek 86 (2004), 1-25.
Schisler, D. A., "Formulation of *Bacillus* Spp. for Biological Control of Plant Diseases", Symposium: The Nature and Application of Biocontrol microbes: *Bacillus* spp., (Feb. 24, 2004), 5 pgs.
Sticklen, Mariam, B., "Plant Genetic Engineering for Biofuel Production: Towards Affordable Cellulosic Ethanol", Nature Reviews: Genetics vol. 9 (Jun. 2008), 433-443.
Yang, Jungwook, "Rhizosphere Bacteria Help Plants Tolerate Abiotic Stress", Trends in Plant Science vol. 14 No. 1 (2009), 1-4.
Bais, Harsh, "Root Secreted Chemical Mediation in Beneficial Plant-Microbe Interactions," Grant Abstract, Grant #0814477 [online]. National Science Foundation; Division of Integrative Organismal Systems (IOS), project dates Aug. 15, 2008 to Jan. 31, 2012 [retrieved on Jan. 15, 2013]. Retrieved from the Internet: <http://www.nsf.gov/awardsearch/showAward?AWD_ID=0814477&HistoricalAwards=false>; 3 pgs, 2012.
Chapman, "A little collaboration grows a long way," Oct. 2010 *University of Delaware Research: Eco-Innovation* vol. 2/No. 1; cover page, table contents, and p. 6. Available on the Internet: <http://www.udel.edu/researchmagazine/issue/vol2_no1_enviro/daretobefirst.html#dare2>, 2010.
Chapman, "Innovation on the rise," Oct. 2010 *University of Delaware Research: Eco-Innovation* vol. 2/No. 1; cover page, table contents, and p. 7. Available on the Internet: <http://www.udel.edu/researchmagazine/issue/vol2_no1_enviro/daretobefirst.html#dare2>, 2010.
Kumar et al., "Rhizobacteria *Bacillus subtilis* restricts foliar pathogen entry through stomata," Nov. 2012 Plant J. 74:694-706. Available online on Sep. 24, 2012.
Melotto et al., "Role of stomata in plant innate immunity and foliar bacterial diseases," Sep. 2008 *Annu. Rev. Phytopathol.* 46:101-122. Author manuscript available online [retrieved on Jan. 15, 2013]. Retrieved from the Internet: <http://www.ncbi.nlm.nih.gov/pmc/articles/PMC2613263/pdf/nihms-82702.pdf>; 27 pages, 2013.
Pare, Paul, "Natural Product Chemistry and Mechanisms of Flavonoid Oxidation," Grant Abstract, Grant No. D-1478 [online]. The Welch Foundation, project dates unknown [retrieved on Jan. 15, 2013]. 2011 Annual Report and Supplement (including abstract D-1478) retrieved from the Internet: <http://www.welch1.org/newsroom-and-reports>; cover page, and pp. 12 and 79, 2013.
"Recruit," in *Merriam-Webster Dictionary*. Available online [retrieved on Jan. 25, 2013]. Retrieved from the Internet: <http://www.merriam-webster.com/dictionary/recruit>; 1 pg, 2013.
Rudrappa et al., "Root-Secreted Malic Acid Recruits Beneficial Soil Bacteria," Nov. 2008 *Plant Physiology* 148:1547-1556. Available online on Sep. 26, 2008.
Rudrappa et al., Supplemental Data for "Root-Secreted Malic Acid Recruits Beneficial Soil Bacteria," Nov. 2008 *Plant Physiology* 148:1547-1556. Available online on Sep. 26, 2008.
Rudrappa et al., "The rhizobacterial elicitor acetoin induces systemic resistance in *Arabidopsis thaliana*," Mar./Apr. 2010 *Communicative & Integrative Biology* 3(2):130-138. Submitted on Jul. 9, 2009; revised and accepted on Nov. 9, 2009.
Non Final Office Action issued Mar. 7, 2012, U.S. Appl. No. 13/037,880.
Amendment and Response filed Jun. 6, 2012, U.S. Appl. No. 13/037,880.
Final Office Action issued Jun. 28, 2012, U.S. Appl. No. 13/037,880.
Choudhary et al., Interactions of *Bacillus* spp. and Plants—With Special Reference to Induced Systemic Resistance (ISR), *Microbiological Research*, 164 (2009), 493-513.
Badri et al., Regulation and Function of Root Exudates, *Plant, Cell and Environ.*, 32 (2009), 666-81.
Rudrappa et al., Root-Secreted Malic Acid Recruits Beneficial Soil Bacteria, *Plant Physiology*, vol. 148 (2008), pp. 1547-1556, Supplemental Data. Retrieved from the Internet: http://www.ncbi.nlm.nih.gov/pmc/articles/PMC2577262/bin.pp.108.127613_index.html, 4 pgs., epub date Sep. 2008.
Ryu et al., Bacterial Volatiles Promote Growth in *Arabidopsis*, Proceedings of the National Academy of Sciences of the United States of America, vol. 100, No. 8 (2003), pp. 4927-4932.

\* cited by examiner

METHODS FOR PROMOTING PLANT HEALTH

CROSS-REFERENCE TO RELATED APPLICATIONS

This application claims priority to application Ser. No. 61/168,778, filed Apr. 13, 2009, which is incorporated herein by reference in its entirety for all purposes.

STATEMENT OF GOVERNMENT SUPPORT

This invention was made with government support under Grant No. IOS-0814477 awarded by the National Science Foundation. The government therefore has certain rights in the invention.

FIELD OF THE INVENTION

The present invention relates to methods for promoting the health of a plant. In particular, embodiments of the present invention relate to increasing pathogen resistance in aerial parts of a plant.

BACKGROUND OF THE INVENTION

Plants are constantly challenged by a plethora of disease-causing microorganisms. To counter the onslaught of infections by pathogens, plants have evolved a combination of constitutive and inducible defense responses.

Beneficial soil bacteria confer immunity against a wide range of foliar diseases by activating plant defenses, thereby reducing a plant's susceptibility to pathogen attack. Many bacterial and fungal pathogens are not restricted to infecting aerial or root tissues exclusively. As such, communication between aboveground and belowground components can confer a survival advantage and potentially prevent diseases. While considerable data exist on the occurrence of aboveground/belowground communication in the case of plant herbivory, evidence of similar phenomena in plant-pathogenic bacteria interactions is lacking.

A number of biocontrol bacteria, also known as plant growth promoting rhizobacteria (PGPR), protect plants from soil-borne pathogens by antagonistic mechanisms (Bais et al., 2004; Cavaglieri et al., 2005). Such bacteria colonizing on plant roots can also induce systemic resistance in aerial plant parts, which are spatially separated from the inducing PGPR (Ryu et al., 2004). This mechanism of induction of systemic resistance by root colonizing rhizobacteria in aerial plant parts is referred to as induced systemic resistance (ISR).

Plants use an array of metabolites to defend themselves against harmful organisms and to attract others that are beneficial. Despite progress toward understanding the symbiotic plant-microbe interactions, little headway has been made in identifying the genetic and biochemical changes responsible for the attraction of non-symbiotic rhizospheric microbes to plants. Although evidence exists for intraplant communication, to date there have been no reports demonstrating whether plants exude specific chemical signals through their roots to attract beneficial bacteria in the rhizosphere.

Furthermore, it is unknown whether shoot infection by pathogenic bacteria induces recruitment of beneficial rhizobacteria to the root surface. Links between interorganism signaling under distress conditions, especially between aboveground and belowground tissues, are poorly understood. Such signaling, although potentially complex due to the involvement of significant physical distances, may be an important and effective strategy in plant defense that has thus far been overlooked.

SUMMARY OF THE INVENTION

The present invention provides methods for promoting the health of a plant. In particular, embodiments of the present invention provide methods for increasing pathogen resistance in aerial parts of a plant.

An embodiment of the present invention provides a method for promoting the health of a plant growing in a soil portion, comprising administering a malate to the plant or the soil portion in an amount effective to recruit plant growth promoting rhizobacteria (PGPR) to the plant. Preferably, L-malic acid is administered to the plant or soil portion in substantially pure isomeric form. Administration of malate promotes biofilm formation of PGPR on the plant's roots, and entry of foliar pathogens through stomatal pores present in the leaves is restricted due to such biofilm formation.

In another embodiment, the present invention provides a method for promoting the health of a plant growing in a soil portion, comprising administering Bacillus subtilis FB17 to the soil portion in an amount effective to recruit PGPR to the plant, wherein the Bacillus subtilis FB17 cause guard cells of the plant to close, thereby restricting pathogen entry into foliar parts of the plant.

In another embodiment, the present invention provides a method for promoting the health of a plant growing in a soil portion, comprising administering acetoin to the plant or the soil portion in an amount effective to increase pathogen resistance in aerial parts of the plant.

It is to be understood that both the foregoing general description and the following detailed description are exemplary, but not restrictive, of the invention.

DETAILED DESCRIPTION OF THE INVENTION

Beneficial soil bacteria confer immunity against a wide range of foliar diseases by activating plant defenses, thereby reducing a plant's susceptibility to pathogen attack. A number of biocontrol bacteria, also known as plant growth promoting rhizobacteria (PGPR), protect plants from soil-borne pathogens. Such bacteria colonizing on the roots can also induce systemic pathogen resistance in aerial plant parts, such as leaves, which are spatially separated from the inducing PGPR. (Ryu et al., 2004) This mechanism of induction of systemic resistance by root colonizing rhizobacteria in aerial plant parts is referred to as induced systemic resistance (ISR).

Beneficial rhizobacteria are capable of activating plant defenses and mitigating the impact of foliar diseases; however, evidence of a plant's ability to recruit these beneficial bacteria has previously been lacking. Applicants have discovered new biochemical evidence that malic acid (MA) secreted from the roots of plants selectively signals and recruits plant growth promoting rhizobacteria (PGPR). In particular, applicants have demonstrated that MA secreted from roots of *Arabidopsis thaliana* (*Arabidopsis*) selectively signals and recruits the beneficial rhizobacterium *Bacillus subtilis* FB17 (FB17) in a dose-dependent manner.

Root secretions of MA are induced by the foliar pathogen *Pseudomonas syringae* pv tomato (Pst DC3000) and elevated levels of MA promote binding and biofilm formation of FB17 on *Arabidopsis* roots. Applicants used the plant pathogen *Pseudomonas syringae* pv tomato (Pst DC3000)-*Arabidopsis* and *B. subtilis* strain FB17 model systems to demonstrate that Pst DC3000-infected *Arabidopsis* foliage relay chemical signals below ground through root secretions. The root-secreted chemical specifically attracts and enhances FB17 root binding and biofilm formation on infected seedlings.

It has been observed that FB17 colonizes and forms continuous biofilms on the roots of *Arabidopsis* plants aerially infected with Pst DC3000. Biofilms are communities of bacteria that are morphologically and physiologically differentiated from free-living bacteria; the process of biofilm formation starts at the late exponential phase of bacterial growth. The demonstration that roots selectively secrete MA and effectively signal beneficial rhizobacteria establishes a regulatory role of root metabolites in recruitment of beneficial microbes, and underscores the breadth and sophistication of plant-microbial interactions.

As discussed above, applicants have discovered that malic acid drives the recruitment of beneficial microbes leading to disease resistance in plants. Plant roots secrete malic acid as a compound to recruit beneficial microbes, specifically *Bacillus subtilis*, which induces resistance in plants against various foliar pathogens. Malic acid supplementation in soil with crop plants may lead to recruitment of beneficial microbes and also disease resistance. The present invention therefore provides new methods for promoting the health of a plant, particularly for increasing pathogen resistance in aerial parts of a plant, i.e., by inducing systemic resistance to pathogens.

One aspect of the invention provides a method for promoting the health of a plant growing in a soil portion comprising administering a malate to the plant or the soil portion in an amount effective to recruit PGPR to the plant. As used herein, a "plant" may comprise any type of plant, including, for example, *Arabidopsis thaliana*. Additional examples of plants may include crop plants, such as corn, tomato plants, or cucumber plants. A "malate" refers to malic acid, as well as salts and esters thereof, e.g., sources or precursors of malic acid. According to the invention, the malate may be administered directly to any part of the plant, either above ground or below ground (e.g., the plant's roots or leaves). Alternatively, the malate may be administered to a soil portion in which the plant is growing. As used herein, a "soil portion" refers to the soil directly surrounding the plant's roots, i.e., a portion of soil into which the plant's roots extend or partially extend. In a preferred embodiment, L-malic acid in substantially pure isomeric form (e.g., malic acid containing at least about 90% or at least about 95% of the L isomer of malic acid) is administered to the plant or the soil portion in an amount effective to recruit PGPR to the plant. The recruitment of PGPR induces biofilm formation on the plant's roots, thereby increasing pathogen resistance in aerial parts of the plant (e.g., foliar resistance).

Applicants have also discovered that rhizobacteria intervene with a plant's guard cell functioning to restrict foliar pathogen entry. The entry of a foliar pathogen (e.g., *Pseudomonas syringae* p.v DC3000) through the stomatal pores present in the leaves is restricted due to the root colonization by beneficial microbe *Bacillus subtilis* FB17. Applicants have tested the results in *Arabidopsis thaliana* by showing that the pathogen entry can be restricted by the addition of the beneficial microbe. Applicants also discovered that even when the plants were previously infected by the pathogen DC3000, the addition of the beneficial microbe causes the stomatal pores to close which prevents further pathogen entry and reduces disease symptoms in the infected plants.

Another aspect of the invention therefore provides a method for promoting the health of a plant growing in a soil portion, comprising administering *Bacillus subtilis* FB17 to the soil portion in an amount effective to recruit PGPR to the plant, wherein the *Bacillus subtilis* FB17 cause guard cells of the plant to close, thereby restricting pathogen entry into foliar parts of the plant. Preferably, the plant is root inoculated or seed inoculated with FB17. Root or seed inoculation provides advantages over the alternative method of applying *B. subtilis* directly to aerial parts of the plants (e.g., plant leaves). Applying *B. subtilis* directly to the aerial parts of the plant, such as by aerially spraying *B. subtilis* onto the plant, can have harmful or toxic effects on the surrounding environment. Thus, root or seed inoculation provides a safer method for administering the beneficial microbe to a plant, as the surrounding air and foliage are less likely to come into contact with *B. subtilis*. As used herein, "guard cells" refer to specialized cells located within aerial parts of a plant (e.g., leaves or stems) which control the opening and closing of a plant's stomatal pores, thereby controlling the plant's gas exchange and water loss.

Applicants have also discovered that acetoin, a volatile organic compound produced by *B. subtilis*, protects plants from pathogen infection. In particular, applicants found that exogenous application of acetoin (3-hydroxy-2-butanone) triggers induced systemic resistance and protect plants against DC3000 pathogenesis. Acetoin-treated *A. thaliana* plants displayed enhanced resistance against DC3000. Another aspect of the invention therefore provides a method for promoting the health of a plant growing in a soil portion, comprising administering acetoin to the plant or the soil portion in an amount effective to increase pathogen resistance in aerial parts of the plant.

EXAMPLES

Examples (1)-(8) relate to the use of malate for improving plant health. Examples (9)-(13) relate to the use of acetoin for improving plant health.

(1) Rhizobacteria Colonization of Roots Stimulated by Leaf Pathogen.

To probe how plant pathogen attack may influence the recruitment of beneficial rhizosphere bacteria, root symbiont colonization was measured in the presence and absence of a foliar pathogen, Twenty-day-old *Arabidopsis* plants were rhizoinoculated with FB17. Subsequently, the plants were infected with Pst DC3000 by pressure infiltration into the leaves. By 5 d postinoculation, leaves infected by Pst DC3000 stimulated biofilm formation of the beneficial rhizobacteria FB17 both qualitatively as determined by confocal microscopy and quantitatively by colony-forming units (CFU). In fact, within 5 d of Pst DC3000 leaf inoculation, a 4-fold increase in FB17 colonization was observed in the roots compared with mock or nonpathogenic *P. syringae* pv *phaseolicola* (NPS3121) treatments [$F(3,20)=114.5$; $P<0.05$]. This observation that aerial infection with Pst DC3000 caused change in root symbiont colonization implicated root exudate involvement in the beneficial microbe recruitment.

(2) Leaf Infection Induces Malic Acid Root Secretions.

To examine whether leaf infection can trigger changes in the composition of metabolites from root secretions, the root secretions from ecotype Columbia (Col-0) plants subjected to different aerial bacterial infection treatments, such as Pst DC3000, untreated (control), water injected (mock), or treated with nonpathogenic strain NPS3121, were collected. The root secretions were chemically analyzed by HPLC. Profiles of the concentrated root exudates from Pst DC3000-infected plants revealed a peak that exhibited a significant increase under the Pst DC3000 infection regime. The peak was further characterized by liquid chromatography-mass spectrometry analysis and retention time overlap and determined to be malic acid (MA); MA quantification from root exudates of differently treated plants indicated a 7-fold increase [$F_{(3,20)}=212.1$; $P<0.05$] in MA accumulation under Pst DC3000 leaf infection compared to control, mock, and NPS3121 treatments.

(3) FB17 Exhibits Positive MA Chemotaxis.

To evaluate MA's ability to selectively recruit FB17, microbial motility at varying MA doses was measured by capillary chemotaxis assay (Gordillo et al., 2007). FB17 exhibits positive chemotactic behavior in a concentration-dependent manner within the dose range of 5 to 30 µM. The concentration range of 5 to 30 µM falls within the biological titers of MA secreted in planta through the root exudates. The non-natural D-MA, as well as the 2-carbon oxalic acid assayed at the high L-MA response level of 30 µM, exhibited significantly [$F_{(4,25)}=117.17$; $P<0.05$] lower efficacies compared to the natural L-MA form, albeit still significantly higher than the water control with D-MA. To establish whether L-MA specifically chemoattracts FB17, other beneficial bacteria, such as *Pseudomonas fluorescens* strain Pf01 and *Azospirillum brasilense* strain Cd, and pathogenic bacteria, such as Pst DC3000, *Erwinia carotovora* strain AH2, *Agrobacterium rhizogenes* strain Arqua-1, and *Agrobacterium tumefaciens* strain LBA4404, were assayed for MA. Our results revealed none of the bacteria shows any significant motility toward L-MA [$F_{(2,25)}=119.12$; $P<0.05$] compared to FB17, establishing the specific chemotactic role of L-MA in attracting PGPR strain FB17. L-MA showed a dose-dependent chemotactic attraction of FB17; structure-dependent chemotactic attraction of FB17; and bacterial species-specific attraction to MA. Bacterial strains used in the chemotactic assay included *B. subtilis* strain FB17, *A. tumefaciens* strain LBA4404, *E. carotovora* strain AH2, *A. rhizogenes* strain Arqua-1, *A. brasilense* strain Cd, *P. fluorescens* (Pf01), and *P. syringae* (Pst DC3000). Data are the average of six replicates from two experiments conducted separately.

(4) MA Transporter Mutant Fails to Recruit *B. subtilis* onto the Root Surface.

*Arabidopsis* T-DNA knockout mutant Atalmt1 for MA transporter AtALMT1 deficient in root MA secretion (Hoekenga et al., 2006) was assayed to confirm the role of MA secretions in recruiting FB17. The amount of malate secreted from Atalmt1 was highly reduced [$F_{(3,20)}=152.62$; $P<0.05$] either with or without Pst DC3000 aerial infection. Moreover, FB17 failed to colonize the root surface of Atalmt1 under both infected and noninfected conditions as shown by both microscopic root binding and CFU data [$F_{(2,25)}=100.23$; $P<0.05$]. To establish the role of AtALMT1 conclusively, we exploited a previously reported approach (Hoekenga et al., 2006) and generated F1 plants (genetically complemented for AtALMT1) from the cross Atalmt1×Landsberg erecta (Ler-0). The F1 generated lines were subsequently used for FB17 colonization studies under a Pst DC3000 infection regime. As expected, FB17 was able to colonize the F1 line of Atalmt1×Ler-0 in a similar fashion to wild-type Col-0 roots especially when leaf infected with Pst DC3000. In our hands, the Atalmt1×Ler-0 F1 line also restored malate release under Pst DC3000 infection (data not shown) as reported previously for aluminum (Al) treatment (Hoekenga et al., 2006).

(5) Leaf Infection Induces Root AtALMT1 Expression.

To check whether aerial leaf infection with Pst DC3000 transcriptionally regulates AtALMT1 expression, we employed an *Arabidopsis* transgenic line carrying an AtALMT1 promoter::GUS fusion construct (Kobayashi et al., 2007). The 20-d-old AtALMT1 promoter::GUS *Arabidopsis* lines were leaf infiltrated with Pst DC3000, NPS3121, *Pseudomonas aeruginosa* PAO1, *Escherichia coli* OP50, and also roots treated with 4 µM $AlCl_3$ as a positive control. The data showed significantly higher AtALMT1::GUS expression in the treatments with Pst DC3000 leaf infection similar to the $AlCl_3$ positive control in both root central elongation zone and mature region. However, leaf infiltration with other bacteria, such as PAO1, OP50, and nonpathogenic NPS3121, showed no induction. These data indicated that the AtALMT1 expression may be specific to leaf pathogenic interactions.

(6) Plant Infected Root Exudates and L-MA Induce *B. subtilis* Biofilm Operons.

Microscopic analysis demonstrated increased binding and biofilm formation of FB17 on the root surface. To examine whether biofilm formation was transcriptionally regulated by root secretions, we tested a key operon yqxM required for *B. subtilis* biofilm formation. We utilized *B. subtilis* strain Marburg carrying the yqxM-lacZ fusion (NRS1531) to study the transcription. Biofilm operon regulation in the lacZ operon fusion line was monitored for β-galactosidase activity. The treatment with root exudates from Pst DC3000-infected plants resulted in higher induction of the yqxM operon between 6 and 12 h posttreatment when compared to untreated controls. However, the decline in the expression after 9 h may be a feedback response.

In addition to root exudates from aerially infected plants causing induction of the FB17 biofilm operon yqxM, MA alone also elevated expression of the biofilm operon yqxM. However, with the L-MA treatment, activity level was lower and the kinetics response was abbreviated compared to root exudates. Another isomer (D-MA) and the two-carbon unit oxalic acid did not stimulate β-galactosidase activity.

(7) FB17 Root Colonization Triggers ISR and Protects *Arabidopsis* from Pst DC3000 Infection.

To test whether plants associated with FB17 extend protection from disease, we inoculated the FB17 root-colonized *Arabidopsis* plants with the pathogen Pst DC3000. Consistent with our data on FB17 root colonization following Pst DC3000 leaf infection, the root colonization of FB17 resulted in protection of plants from Pst DC3000 infection. The Pst DC3000-infected FB17-colonized plants revealed reduced disease incidence, symptom development (chlorosis), and pathogen multiplication. The results were highly significant ($P<0.05$; t test) compared to the control plants not colonized with FB17 and treated with Pst DC3000.

To further test whether this protection offered by FB17 was due to the induction of ISR, we checked for known systemic resistance markers such as PR1 gene expression and free SA levels in the leaves of FB17 root-colonized plants. We utilized *Arabidopsis* lines carrying PR1::GUS fusions to study the PR1 expression. Plant roots colonized with FB17 showed higher PR1::GUS expression in the leaves on par with leaf SA-treated positive controls compared to uninoculated control plants. Other controls, where plants were root inoculated with OP50 and Pf01, failed to induce PR1::GUS expression in the leaves. Similarly, when free SA levels were analyzed (Scott et al., 2004), the Col-0 plant roots colonized with FB17 showed increased free SA titers compared to plants without FB17 colonization.

(8) *P. fluorescens* (Pf01) Fails to Bind to the Root Surface of Aerially Infected *Arabidopsis* Col-0.

To test the specificity of the *Arabidopsis* FB17 interaction, Pf01 root-inoculated plants were monitored with and without aerial infection. Consistent with chemotaxis assay data, infected plants failed to recruit Pf01 to the root surface as observed previously for FB17. The Pst DC3000-infected Col-0 plants showed poor binding of Pf01, indistinguishable from the untreated and Pf01-only treatments. Further, the Pf01 root inoculation failed to protect plants from Pst DC3000 infection. This result suggested that plants specifically engaged with FB17 under foliar bacterial infection.

(9) Acetoin, a Volatile Organic Compound (VOC) Produced by B. subtilis, Protects Plants from DC3000 Infection.

As it has been reported that *B. subtilis* is a prolific producer of small molecular weight compounds, including various VOC blends (Ryu et al. 2003), we examined whether the elicitation of defense pathways can be mediated by a bacterial volatile organic compound that protects plants from DC3000 infection. To address this question, we tested the effect of already reported *B. subtilis* volatile metabolite acetoin. In this experiment, we included acetoin in the magenta boxes in which *Arabidopsis* plants were grown. Plants were exposed to acetoin treatment followed by leaf inoculation with DC3000 simultaneously; post-infection plants were incubated with acetoin for an additional 5 days. Interestingly, the plants subjected to volatile treatment developed significantly lower disease symptoms when compared to untreated controls. A significantly lower percent disease incidence, calculated as the ratio of total number of leaves that developed symptoms to total number of leaves inoculated (Katagiri 1 et al. 2002), and lower DC3000 CFUs ($P<0.05$, t-test) were recorded from the leaves of the plants subjected to acetoin treatment. Since DC3000 was not susceptible to direct antimicrobial acetoin (1 ml of 10 mM stock~88 μg) treatments from broth microdilution assays, acetoin appears to be effectively activating plant defenses against aerially infected DC3000.

(10) Acetoin Biosynthetic Mutants Fail to Trigger ISR.

To further probe the role of acetoin in induction of ISR in *Arabidopsis* against DC3000 infections, we employed *B. subtilis* strains BSIP1173, and BSIP1174 (Ramos et al. 2000). The strains BSIP1174 and BSIP1173 are impaired in acetoin production because of an insertional mutation in the acetolactate synthase (operon that controls the penultimate step in acetoin formation i.e., pyruvate to acetolactate conversion) and acetolactate dehydrogenase, the enzymatic step that converts acetoin to 2,3-butanediol (Ramos et al. 2000), thus making the mutant strains accumulate reduced levels of acetoin and 2,3-butanediol when compared to wild type strains BS168, GB03 and BSIP1171 (acetoin overproducing strain) (Ramos et al. 2000; Ryu et al. 2004). The mutant and over-expressing strains were tested and compared against wild type strains BS168 (parental strain), GB03 and FB17 for their effect on DC3000 infection in *A. thaliana*. All of the wild type and mutant strains, including the over-expressing strain BSIP1171, showed similar root colonization on aerially infected DC3000 *Arabidopsis* Col-0 plants but the acetoin mutant strains (BSIP1173 and BSIP1174) failed to protect the plants from DC3000 infection. A significantly higher symptom development, percent disease incidence ($F_{(6,43)}=153.1$, $P<0.05$) and DC3000 CFUs ($F_{(6,43)}=125.3$, $P<0.05$) was recorded from the plant roots that were inoculated with acetoin biosynthetic mutant strains compared to the plant roots inoculated with wild type *B. subtilis* strains. In summary, our data shows that acetoin released from the *B. subtilis* augments plant defense against aerial DC3000 infections. We also show that acetoin is not important for the root binding phenotype as the acetoin mutants' biofilms were indistinguishable from the parental wild type strains (Rudrappa et al. 2007, 2008).

(11) FB17-inoculated *A. thaliana* Mutants Exhibit Differential Defense Responses.

To determine the involvement of SA and ET/JA pathways mediated by FB17, we employed an SA deficient *Arabidopsis* line (NahG) and ET/JA (etr1-3, jar1-1) *Arabidopsis* signaling mutants treated with FB17 and infected with DC3000. No significant difference was observed between the *B. subtilis* root inoculated and un-inoculated NahG plants in terms of disease symptom development, and DC3000 CFUs from inoculated leaves. In contrast, a JA component mutant jar1-1 showed reduced DC3000 CFU ($F_{(2,19)}=231.2$, $P<0.05$) and disease symptoms indicative of chlorosis post FB17 treatment. The ET pathway compromised mutant, etr1-3 revealed a similar phenotype as shown previously with NahG plants, indicating no enhanced disease resistance post FB17 treatment and DC3000 infection. Together, these data suggest that *B. subtilis* FB17 induced systemic resistance is NPR-1 dependent and requires SA and ET. Further to test whether acetoin also requires NPR1, SA and ET components to induce resistance against DC3000, infections were carried out in a similar experiment as described earlier for FB17 except that the FB17 was replaced with acetoin treatment. Acetoin failed to protect SA deficient NahG and ethylene mutant etr1-3 plants from DC3000 infection, whereas a significantly reduction in DC3000 multiplication in terms of CFUs ($F_{(2,29)}=231.2$, $P<0.05$) was observed with wild type Col-0 and jasmonic acid mutant Jar1-1. These results correlated well with the earlier results with FB17 treatment and indicated that the *B. subtilis* derived-acetoin functions through NPR1-dependent pathway and required SA and ET components to induce resistance against DC3000 infections.

(12) *B. subtilis* and Acetoin Effects Key Genes 1 in the SA and JA/ET Pathways.

Our earlier experiments indicated that FB17-induced resistance against DC3000 was governed by SA and ET pathways. Our results show that the compromised defense mutants in these respective pathways failed to exhibit enhanced resistance against DC3000 in FB17 treated plants. To further confirm the involvement of NPR1, we studied the effect of FB17 root colonization on PR1 gene expression using an *A. thaliana* Col-0 transgenic reporter line for PR1::GUS. Surprisingly, we observed higher PR1::GUS expression in plants that were root inoculated with FB17 compared to control untreated plants. The PR1::GUS expression was higher in the aerial parts compared to the root system in the FB17 treated plants. The plants treated with other bacteria such as *Pseudomonas fluorescens* (Pfo-1) and *Escherichia coli* (0P50) revealed modest PR1 expression compared to FB17 treatment. *Arabidopsis* leaves sprayed with SA also showed higher PR1 expression while the root treated plants showed much less PR1 expression. As our results show that acetoin treated *Arabidopsis* plants displayed enhanced resistance against DC3000, we examined whether acetoin induced expression of key defense genes. To this end, we employed the PR1::GUS *Arabidopsis* lines; treatment of *Arabidopsis* PR1::GUS plants with acetoin showed enhanced PR1 expression compared to the untreated plants. Acetoin treated *Arabidopsis* plants also revealed PR1 expression patterns similar to FB17 treatments. Our data with the disease compromised mutants showed that FB17 mediated ISR, against DC3000, is NPR1-dependent and requires ET/SA. Further, we estimated the free SA levels, and our results showed significantly ($F(8, 55)=175.2$, $P=0.05$) higher SA levels in the leaves of the plants that were root inoculated with FB17 compared to the control untreated plants. Negative controls such as plant roots treated with other rhizobacteria *P. aeruginosa* (PA01) and Pfo-1 showed no induction in free SA levels. Interestingly, acetoin treatment also enhances the total free SA level ($F_{(2,19)}=131.2$, $P<0.05$) in *Arabidopsis* plants.

To further confirm that a FB17 component, acetoin, mediates this response we analyzed the defense genes PDF1.2 and Jin1 whose expression depends on functional ET and JA pathways. Our RT-PCR data shows that acetoin and FB17 treated *Arabidopsis* plants express more PDF1.2 and PR1 transcripts in leaves compared to the mock inoculated plants. Surprisingly, our results negated PDF1.2 and PR1 transcript expression in roots under FB17 treatments. Further, co-inoculations of DC3000 with *B. subtilis* acetoin biosynthetic mutants (BPS1173 and BPS1174) also showed similar results confirming the role of NPR-1. These results establish the involvement of this FB17 derived volatile component in mediating defense responses against DC3000 through NPR1 and ET dependent pathways.

(13) *P. fluorescens* (Pf01) fails to bind to root surface of aerially infected *Arabidopsis* Col-0 and 13 hence shows no protection effect.

In order to test the specificity of the *A. thaliana-B. subtilis* interaction, we used another well known PGPR *P. fluorescens* (Pf01) for root inoculation of *A. thaliana* Col-0 and determined its effect on aerial infection. The DC3000 infected Col-0 plants showed poor binding of Pf0-1, which was indistinguishable from the untreated and Pf0-1 only treatments. This result suggested that the plants may be specifically engaged with *B. subtilis* under foliar pathogen infections. In accordance with the root binding data, other parameters such as disease symptom development, percent disease incidence and DC3000 CFUs from inoculated leaves showed no significant difference (t-test) between Pf01 inoculated and un-inoculated plants.

Although illustrated and described above with reference to certain specific embodiments, the present invention is nevertheless not intended to be limited to the details shown. Rather, various modifications may be made in the details within the scope and range of equivalents of the claims and without departing from the invention.

REFERENCES

Bais H P, Fall R, Vivanco J M (2004) Biocontrol of *Bacillus subtilis* against infection of *Arabidopsis* roots by *Pseudomonas syringae* is facilitated by biofilm formation and surfactin production. Plant Physiol 134: 307-319.

Cavaglieri L, Orlando J, Rodriguez M I, Chulze S, Etcheverry M (2005) Biocontrol of *Bacillus subtilis* against *Fusarium verticillioides* in vitro and at the maize root level. Res Microbiol 156: 748-754.

Gordillo F, Chavez F P, Jerez C A (2007) Motility and chemotaxis of *Pseudomonas* sp. B4 towards polychlorobiphenyls and chlorobenzoates. FEMS Microbiol Ecol 60: 322-328.

Hoekenga O A, Maron L G, Pineros M A, Cancado G M A, Shaff J, Kobayashi Y, Ryan P R, Dong B, Delhaize E, Sasaki T, et al (2006) AtALMT1, which encodes a malate transporter, is identified as one of several genes critical for aluminum tolerance in *Arabidopsis*. Proc Natl Acad Sci USA 103: 9738-9743.

Katagiri F, Thilmony R, He S Y eds (2002) The *Arabidopsis-Pseudomonas Syringae* 20 Interaction American Soc Plant Biol, Rockville, Md.

Kobayashi Y, Hoekenga O A, Itoh H, Nakashima M, Saito S, Shaff J E, Maron L G, Piñeros M A, Kochian L V, Koyama H (2007) Characterization of AtALMT1 expression in aluminum-inducible malate release and its role for rhizotoxic stress tolerance in *Arabidopsis*. Plant Physiol 145: 843-852.

Ramos H C, Hoffmann T, Marco M, Hafed N, Presecan-Siedel E, Dreesen O, Glaser P, Jahn D (2000) Fermentative metabolism of *Bacillus subtilis*: Physiology and regulation of gene expression. 3 Bacteriol 182:3072-3080.

Rudrappa, T, Quinn, W J, Stanley-Wall, N R, Bais, H P (2007) A degradation product of the salicylic acid pathway triggers oxidative stress resulting in down-regulation of *Bacillus subtilis* biofilm formation on *Arabidopsis thaliana* roots. Planta 226:283-97.

Rudrappa T, Czymmek K J, Paré P W, Bais H P (2008) Root secreted malic acid recruits beneficial soil bacteria. Plant Physiol 148: 1547-56.

Ryu C M, Farag M A, Hu C H, Reddy M S, Kloepper J W, Pare P W (2004) Bacterial volatiles induce systemic resistance in *Arabidopsis*. Plant Physiol 134: 1-10

Scott I M, Clarke S M, Wood J E, Mur L A J (2004) Salicylate accumulation inhibits growth at chilling temperature in *Arabidopsis*. Plant Physiol 135: 1040-1049.

We claim:

1. A method for promoting the health of a crop plant growing in a soil portion, comprising administering L-malic acid to the soil portion in an amount effective to recruit *Bacillus subtilis* FB 17 to the plant.

2. The method according to claim 1, wherein recruitment of *B. subtilis* FB 17 PGPR induces biofilm formation on the plant's roots and increases pathogen resistance in aerial parts of the plant.

3. The method according to claim 1, comprsing administering the L-malic acid in substantially pure isomeric form.

4. The method according to claim 2, wherein the pathogen resistance in aerial parts of the plant comprises foliar resistance to pathogens.

5. The method according to claim 4, wherein the pathogens comprise *Pseudomonas syringae* pv tomato.

6. The method according to claim 1, wherein the crop plant is selected from the group consisting of corn, tomato plants, and cucumber plants.

* * * * *

UNITED STATES PATENT AND TRADEMARK OFFICE
CERTIFICATE OF CORRECTION

PATENT NO.       : 8,551,919 B2                                Page 1 of 1
APPLICATION NO.  : 12/758361
DATED            : October 8, 2013
INVENTOR(S)      : Bais et al.

It is certified that error appears in the above-identified patent and that said Letters Patent is hereby corrected as shown below:

In the Claims

At column 10, line 34, claim 1, delete "FB 17" and insert --FB17--;

At column 10, line 36, claim 2, delete "FB 17 PGPR" and insert --FB17--.

Signed and Sealed this
Third Day of December, 2013

Margaret A. Focarino
*Commissioner for Patents of the United States Patent and Trademark Office*